(12) United States Patent
Liu et al.

(10) Patent No.: US 9,226,731 B2
(45) Date of Patent: Jan. 5, 2016

(54) OPTICALLY GUIDED NEEDLE BIOPSY SYSTEM USING MULTI-MODAL SPECTROSCOPY IN COMBINATION WITH A TRANSRECTAL ULTRASOUND PROBE

(75) Inventors: Hanli Liu, Arlington, TX (US); Vikrant Sharma, Arlington, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 40 days.

(21) Appl. No.: 13/224,218

(22) Filed: Sep. 1, 2011

(65) Prior Publication Data

US 2011/0319759 A1 Dec. 29, 2011

Related U.S. Application Data

(63) Continuation-in-part of application No. 12/600,975, filed as application No. PCT/US2008/064429 on May 21, 2008, now Pat. No. 8,649,849.

(60) Provisional application No. 60/939,239, filed on May 21, 2007, provisional application No. 61/379,699, filed on Sep. 2, 2010.

(51) Int. Cl.
| | | |
|---|---|---|
| *A61B 10/02* | (2006.01) | |
| *A61B 8/08* | (2006.01) | |
| *A61B 8/12* | (2006.01) | |
| *A61B 5/00* | (2006.01) | |

(52) U.S. Cl.
CPC ............ *A61B 10/0241* (2013.01); *A61B 5/0071* (2013.01); *A61B 5/0075* (2013.01); *A61B 5/0084* (2013.01); *A61B 5/4887* (2013.01); *A61B 8/085* (2013.01); *A61B 8/12* (2013.01)

(58) Field of Classification Search
CPC ............ A61B 10/0241; A61B 5/0071; A61B 5/0075; A61B 5/0084; A61B 5/4887; A61B 8/085; A61B 8/12
See application file for complete search history.

(56) References Cited

U.S. PATENT DOCUMENTS

| | | | | |
|---|---|---|---|---|
| 5,398,690 | A  * | 3/1995  | Batten et al. ................... | 600/461 |
| 6,174,291 | B1 * | 1/2001  | McMahon et al. ............. | 600/564 |
| 8,239,139 | B2 * | 8/2012  | Mycek et al. .................... | 702/19 |
| 2004/0054290 | A1 * | 3/2004 | Chance ........................... | 600/473 |
| 2005/0203413 | A1 * | 9/2005 | Fichtinger et al. .............. | 600/461 |
| 2009/0203991 | A1 * | 8/2009 | Papaioannou et al. ......... | 600/421 |
| 2009/0317856 | A1 * | 12/2009 | Mycek et al. .................... | 435/29 |
| 2010/0198080 | A1 * | 8/2010 | Liu et al. ......................... | 600/477 |
| 2012/0245473 | A1 * | 9/2012 | Mycek et al. .................. | 600/479 |

OTHER PUBLICATIONS

Bensalah et al., Optical reflectance Spectroscopy to Differentiate Renal Tumor from Normal Parenchyma; J. Urol.; 179: 2010-2013 (2008).

(Continued)

*Primary Examiner* — Amanda Lauritzen Moher
(74) *Attorney, Agent, or Firm* — Winstead PC (57) ABSTRACT

The present invention includes an apparatus, system and method for detection of tissues, e.g., a cancer, by optical biopsy comprising: a motorized computer-controlled probe holder; a needle-like probe connected to and controlled by the motorized computer-controlled probe holder, the probe comprising an optical and an ultrasound detector; and one or more detector units capable of a broadband light reflectance spectroscopy, an auto fluorescence lifetime measurement, and auto fluorescence spectroscopy measurement.

10 Claims, 7 Drawing Sheets

(56) References Cited

OTHER PUBLICATIONS

Bensalah et al., Optical Reflectance Spectroscopy to Differentiate Benign From Malignant Renal Tumors at Surgery, Urology 73(1), pp. 178-181 (2009).

Bigio et al., Diagnosis of breast cancer using elastic-scattering spectroscopy: preliminary clinical results, Journal of Biomedial Optics (5(2), pp. 221-228 (2000).

Demos, Spectroscopic detection of bladder cancer using near-infrared imaging techniques, Journal of Biomedial Optics 9(4), pp. 767-771 (2004).

Demos et al., Investigation of Near-Infrared Autofluorescence Imaging for the Detection of Breast Cancer, IEEE Journal of Selected Topics in Quantum Electronics, vol. 11 (4), pp. 791-798 (2005).

Giller et al., Use of an intracranial near-infrared probe for localization during stereotactic surgery for movement disorders, J. Neurosurg. 93: 498-505 (2000).

Katika et al., In-Vivo Time-Resolved Autofluorescence Measurements on Human Skin, eScholarship University of California (2006).

Kanick et al., Integration of single-fiber reflectance spectroscopy into ultrasound-guided endoscopic lunc cancer staging of mediastinal lymph nodes, Journal of Biomedical Optics 15(1): 017004-1-017004-8 (2010).

Lin et al., In Vivo Brain Tumor Demarcation Using Optical Spectroscopy, Photochemistry and Photobiology, 73(4): 396-402 (2001).

Mizeret et al., Instrumentation for real-time fluorescence lifetime imaging in endoscopy, Review of Scientific Instruments, 70(12): 4689-4701 (1999).

Utzinger et al., Reflectance Spectroscopy for in Vivo Characterization of Ovarian Tissue, Lasers in Surgery and Medicine, 28: 56-66 (2001).

Salomon et al., The Feasibility of Prostate Cancer Detection by Triple Spectroscopy, European Urology 55: 376-384 (2009).

Sharma et al., Optical Reflectance Spectroscopy for Detection of Human Prostate Cancer, 31st Annual International Conference of the IEEE EMBS, pp. 118-121 (2009).

Sharma et al., A Dual-Modality Optical Biopsy Approach for in Vivo Detection of Prostate Cancer in Rat Model, Journal of Innovative Optical Health Sciences, 4(3): 269-277 (2011).

Sharma et al., Quantification of light reflectance spectroscopy and its application: Determination of hemodynamics on the rat spinal cord and brain induced by electrical stimulation, Neuroimage, 56(3): 1316-1328 (2011).

Xiao et al., Autofluorescence imaging analysis of gastric cancer, Chinese Journal of Digestive Diseases, 3: 95-98 (2002).

Zonios et al., Modeling diffuse reflectance from semi-infinite turbid media: application to the study of skin optical properties, Optics Express, 14(19): 8661-8774 (2006).

* cited by examiner

OPTICALLY GUIDED NEEDLE BIOPSY SYSTEM USING MULTI-MODAL SPECTROSCOPY IN COMBINATION WITH A TRANSRECTAL ULTRASOUND PROBE

CROSS-REFERENCE TO RELATED APPLICATIONS

This application claims the benefit of U.S. Provisional Patent Application Ser. No. 61/379,699, filed Sep. 2, 2010, and incorporated herein by reference in its entirety. This application is a continuation-in-part of application Ser. No. 12/600,975, which is the National Stage of International Application No. PCT/US08/64429, filed May 21, 2008, which claims the benefit under 35 U.S.C. §119(e) of U.S. Provisional Patent Application Ser. No. 60/939,239, filed May 21, 2007.

STATEMENT OF FEDERALLY FUNDED RESEARCH

This invention was made with U.S. Government support under Contract No. W81XWH-09-1-0406 awarded by the Department of Defense. The government has certain rights in this invention.

TECHNICAL FIELD OF THE INVENTION

The present invention relates in general to the field of cancer tissue detection, and more particularly, to an optically guided needle biopsy system and method.

BACKGROUND OF THE INVENTION

Without limiting the scope of the invention, its background is described in connection with prostate cancer.

Prostate cancer is the second leading cause of cancer death among American men, after lung cancer. Every year, more than 180,000 new cases of prostate cancer are reported and approximately 29,000 men die of the cancer of the prostate. In order to have the best and timely treatments, early diagnosis is the key. The current gold standard for diagnosis is needle biopsy, which has major drawbacks and can still miss about 30% of existing carcinomas.

Hence an improved system, apparatus and method would be advantageous for the early and accurate detection and diagnosis of cancer, particularly prostate cancer.

SUMMARY OF THE INVENTION

An embodiment of the invention is directed to an apparatus for detection of cancer by optical biopsy, the apparatus comprising: a motorized computer-controlled probe holder comprising a probe device, wherein the probe device comprises an ultrasound probe and an optical attachment that is removably connected to the ultrasound probe and controlled by the motorized computer-controlled probe holder, and wherein the optical attachment comprises at least one optical fiber and at least one biopsy needle; an optical system comprising at least two light sources; and one or more detecting units capable of a broadband light reflectance spectroscopy and an auto fluorescence lifetime measurement. In another aspect of the claimed invention, the ultrasound probe is a transrectal ultrasound (TRUS) probe. In another aspect, the spectroscopic detecting unit is capable of at least one of a light scattering spectroscopy, auto-fluorescence spectroscopy and auto-fluorescence life-time measurements. In another aspect, the probe device further comprises a miniaturized step motor connected to the optical attachment and controlled by a computer with a user-friendly graphical user interface (GUI) for data acquisition and automated probe movement.

Another embodiment of the present invention includes a method of detecting a cancer comprising: identifying a patient suspected of having a cancer; and detecting a tissue from the patient suspected of having the cancer, with an apparatus for detection of cancer by optical biopsy.

An embodiment of the invention is directed to a method for inserting a probe device into a cavity wall using a motorized computer-controlled probe holder comprising a probe device, wherein the probe device comprises an ultrasound probe and an optical attachment that is removably connected to the ultrasound probe and controlled by the motorized computer-controlled probe holder, and wherein the optical attachment comprises at least one optical fiber and at least one biopsy needle, the method comprising the steps of: inserting the probe device into a cavity; determining a target location inside the cavity wall; computing a probe device position corresponding to the target location; computing a needle depth corresponding to the target location and the probe device position; positioning the probe device according to the probe device position; and inserting the needle according to the needle depth.

Another embodiment of the invention is directed to a system for imaging of tissue, said system comprising a probe device, wherein the probe device comprises an ultrasound probe and an optical attachment that is removably connected to the ultrasound probe, wherein the optical attachment comprises at least one optical fiber and at least one biopsy needle; an optical system comprising at least two light sources; and one or more spectroscopic detecting units capable of a broadband light reflectance spectroscopy, an auto fluorescence lifetime measurement, and an auto fluorescence spectroscopy.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF PREFERRED EMBODIMENTS

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The purpose of the claimed invention improves the accuracy of prostate cancer diagnosis by using an optically guided needle biopsy system. Currently, needle biopsy, which is the gold standard in prostate cancer diagnosis, is conducted in a random fashion. As a result, more than 30% of cancers are missed by the biopsy. An increase in the number of cores by saturation biopsy (involving 30-80 cores) has been proposed in order to improve the specificity and sensitivity. However, multiple studies have recently reported that there is not much improvement in sensitivity and specificity by saturation biopsy. Therefore, accurately locating the prostate cancer lesions remains a critical challenge.

The claimed invention solves the problem with a lack of navigation during the biopsy procedure by providing a portable, optical system that is compatible with existing systems and thus can be used to guide the prostate biopsy in real time. Although the system is described with respective to prostate cancer detection, the same system can be used for the detection of other cancers including breast cancer and thyroid cancer.

The inventive apparatus for detection of cancer by optical biopsy comprises: a motorized computer-controlled probe holder comprising a probe device, the probe device in turn comprising an ultrasound probe and a removable optical attachment connected to the probe and controlled by the motorized computer-controlled probe holder, wherein the optical attachment comprises an optical fiber and a biopsy needle; and one or more detector units capable of a broadband light reflectance spectroscopy, an auto fluorescence lifetime measurement, and an auto fluorescence spectroscopy.

The optical attachment used in embodiments of the claimed invention is thinner than a conventional biopsy needle, and is used to collect optical signatures from cancerous and non-cancerous prostate tissue. In certain embodiments of the invention, the optical attachment comprises a biopsy needle and an optical fiber located in close proximity to one another within the optical attachment. In some embodiments of the invention, the optical attachment comprises a hollow channel that houses an optical fiber and a biopsy needle. The optical fiber and biopsy needle, although located in close proximity to one another, are separable from one another and may be located at a desired distance from one another within the hollow channel.

In an embodiment of the invention, the optical fiber of the claimed invention is a bifurcated fiber comprising one or more channels that serve transmit the light from the light source to the tissue being examined (source channels) and one or more channels that serve to transmit the light reflected from the tissue being examined (detector channels) In certain embodiments of the invention, a source channel has a diameter ranging from 100 to 200 µm. In other embodiments of the invention, a detector channel has a diameter ranging from 200 to 400 µm.

The component for optical detection can be (a) a steady-state, broadband visible-to-NIR (near infrared) spectrometer, and/or (b) time-dependent autofluorescence life-time measurement unit, and/or (c) time-dependent reflectance measurement unit. The motorized computer-controlled probe holder connects the optical attachment with a minaturized step motor that is controlled by a computer through a clinician-friendly GUI (graphical user interface) for fast data acquisition and automated probe movement.

The optical biopsy system of the claimed invention provides the urologist with a method and system that allows the user to "assess" the prostate tissue during biopsy in real-time. The prostate tissue samples to be biopsied can be optimally selected for improved diagnosis with the system of the present invention, which makes the procedure more accurate, less painful, and less harmful for the patient.

The claimed invention can be used to accurately guide prostate cancer biopsy while being compatible with the current biopsy needles. The claimed invention offers clinicians a high probability to detect early prostate cancer and improves the accuracy of prostate cancer diagnosis. Thus, the rate for under-treatments or over-treatments of prostate cancer is reduced significantly, improving the patients' quality of life.

The present invention provides for (1) the use of optical signatures to diagnose prostate cancer and to guide prostate biopsy; (2) integration of an optical probe with existing ultrasound guided biopsy system; and (3) an optical attachment having an optical fiber and a biopsy needle, coupled to a miniaturized step motor that is controlled by a computer through a clinician-friendly GUI (graphical user interface) for fast data acquisition and automated probe movement; (4) multi-modal instrument integration for optical spectroscopy and auto-fluorescence life-time method to identify positive cancer lesions within the human prostate in vivo during needle biopsy procedures.

An embodiment of the claimed invention is directed to the development of a diagnostic probe that can be used with an existing needle biopsy tool and guide the clinicians to select the biopsy sites in real time for prostate cancer diagnosis.

Optical spectroscopy of tissues can provide spectral finger prints of tissue types and can be used to differentiate cancerous tissues from healthy tissues. In recent years, a variety of spectroscopic approaches, such as elastic light-scattering reflectance, auto-fluorescence, and low-coherent interferometry, have been developed for local detection and diagnosis of various kinds of cancers and tumors.

Light Scattering Spectroscopy (LSS) can be associated with several optical spectroscopic techniques, such as elastic light scattering spectroscopy with un-polarized and polarized light, angle-resolved low-coherence interferometry, and coherent backscattering spectroscopy. All of these techniques utilize small-distance light reflectance measurements and examine changes in spectral, angular, and polarization characteristics of light scattered from tissue. LSS can differentiate tissue types and diagnose tissue abnormalities at the local measurement site, with a penetration depth of 1-2 millimeter using unpolarized near infrared light.

Fluorescence emission, in contrast to light scattering methods, is shifted towards longer wavelengths as compared to the impinging illumination. This allows using cut-off filters and monochromators to observe the phenomenon in a practically dark background. Fluorescence studies fall into two categories: a steady-state and time-resolved modes. In the steady-state mode, the intensity of emission is being collected as function of wavelength, resulting in fluorescence spectra that are characteristic for studied chromophores. Autofluorescence spectrum of tissue with UV/visible excitation may contain components related to tryptophan elastin, NADH, flavins, porphyrins, lipopigments and others. A proper excitation should be used to register emission of one or several particular components.

The intensity of auto-fluorescence of tissue can be also detected as a function of time: the fluorescence signal is delayed as compared to the excitation light, in contrast to the scattering signal. Each fluorophore has its characteristic lifetime, which in addition to the spectra gives another opportunity for fluorescence species differentiation. The advantage of the latter mode is the intrinsic nature of lifetime measurements, independent of the intensity of excitation light, providing clear finger prints for cancer identifications. In particular, time-resolved fluorescence measurements for cancer detection have been conducted in two major areas: (1) fluorescence life-time microscopy and imaging using ex vivo samples and in vivo animal models, and (2) non-invasive breast cancer detection using the frequency-domain approach.

Multi-modal optical measurements that are used in embodiments of the invention are (1) light reflectance spectroscopy (LRS), (2) auto-fluorescence spectroscopy (AFS), and (3) auto-fluorescence life-time measurements (AFLM). These three optical methods are integrated into an optical probe that can be used in vivo in real time during the conventional needle biopsy procedures for optically guided tissue biopsy to accurately diagnose prostate cancer.

In an embodiment of the invention, both LRS and AFLM systems are used to differentiate between cancerous and non-cancerous tissues using a rat prostate cancer model with both ex vivo and in vivo measurements. LRS is used to calculate the absolute concentrations of oxy-hemoglobin, deoxy-hemoglobin and scattering properties of the tissue, while AFLM provided auto-fluorescence lifetime of the tissues by a single-channel, time correlated single photon counting (TCSPC) device. Following data analysis, the efficacy of using these multiple parameters as classifiers for identification of the tumor is tested.

Figure 2:
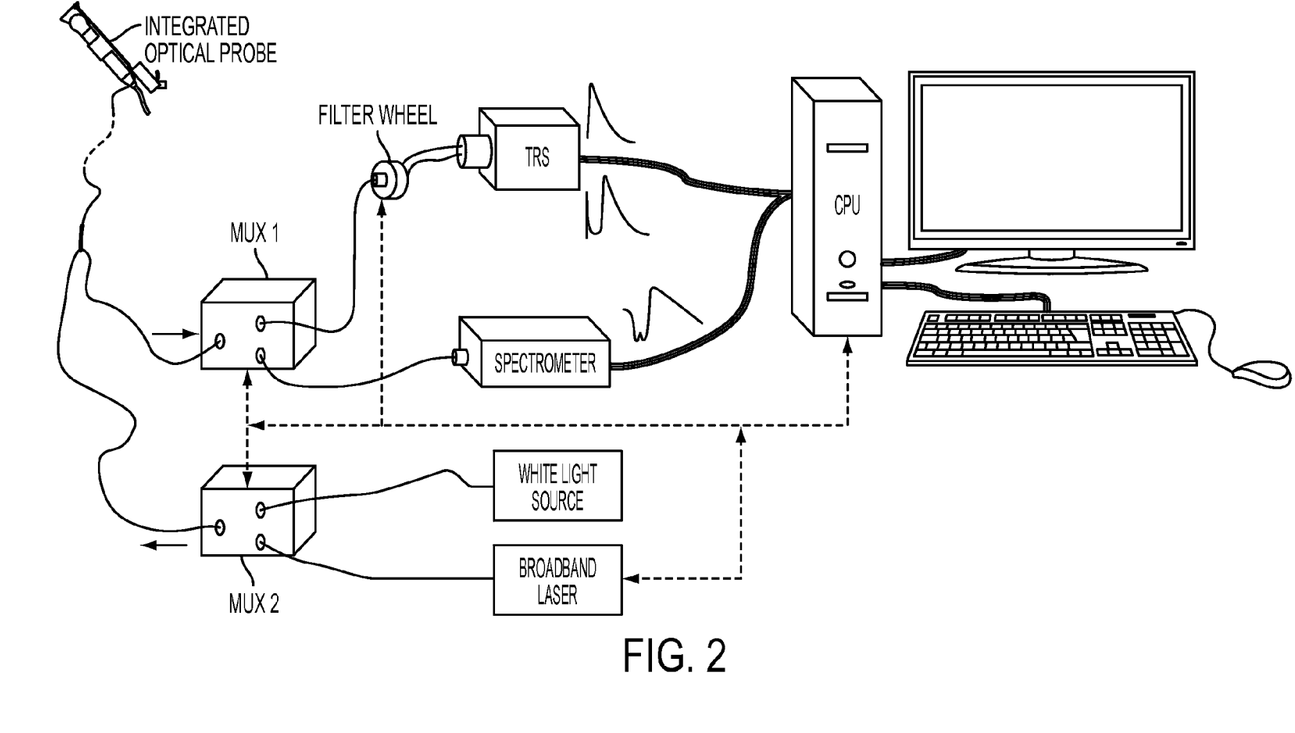
FIG. 2 represents a schematic diagram of a multi-modal spectroscopic system of the invention.

In an embodiment of the invention, the optical attachment incorporates a bifurcated fiber having one fiber channel that acts as a source and a second fiber channel that acts as a detector. As shown in FIG. 2, using one or more optical techniques requires switching of sources and detectors, which can be achieved by using fiber-optic multiplexers for detectors (MUX1) and sources (MUX2). Switching and timing parameters are controlled using data acquisition cards installed in the CPU.

FIG. 2 shows the data acquisition using following 3 techniques:

Broadband Light Reflectance Spectroscopy (LRS): A broadband white light source is used to transmit light into the tissue through MUX1, and the returning light is passed through MUX2 into a single channel broadband (500-850 nm) spectrometer to obtain a reflectance spectrum.

Auto fluorescence Life-Time Measurement (AFLM): A broadband ultrafast pulsed laser source is set to the required repetition frequency using control signals, and the light is passed through MUX2 to the tissue. The returning light is fed though MUX 1 into an ultrafast detector system, which is based on time-resolved spectroscopy (TRS), through a motor controlled filter wheel. The filter wheel contains band pass filters which can be switched using a motor controlled by CPU. The laser source is set to be in the UV to Visible range, and the filter wheel is switched to measure multiple emission wavelengths i.e., $\lambda 1, \lambda 2, \lambda 3 \ldots \lambda n$.

Auto fluorescence spectroscopy (AFS): The light path is similar to LRS except that a set of appropriate filters will be chosen and added in the excitation and emission optical path.

The dashed lines represent the acquisition control which is managed by data acquisition (DAQ) cards in the CPU. Data is acquired using all three techniques as the fiber probe is advanced into the prostate.

Figure 3A:
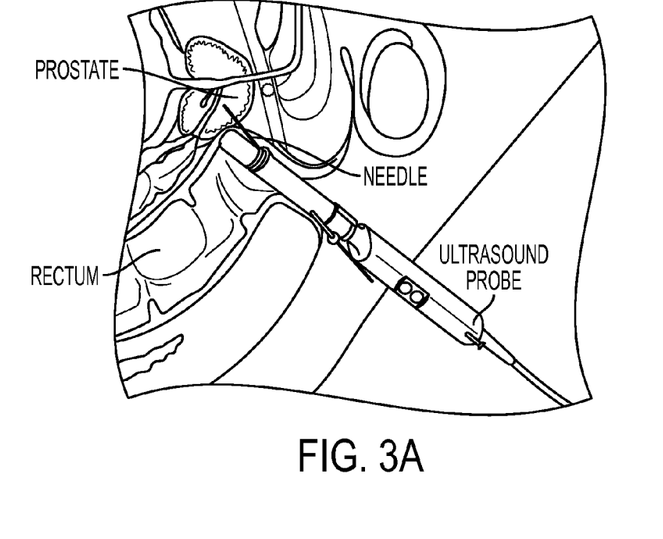
FIG. 3A shows a conventional prostate biopsy procedure using a trans-rectal, side-fire ultrasound probe (TRUS) with a biopsy needle.
Figure 3B:
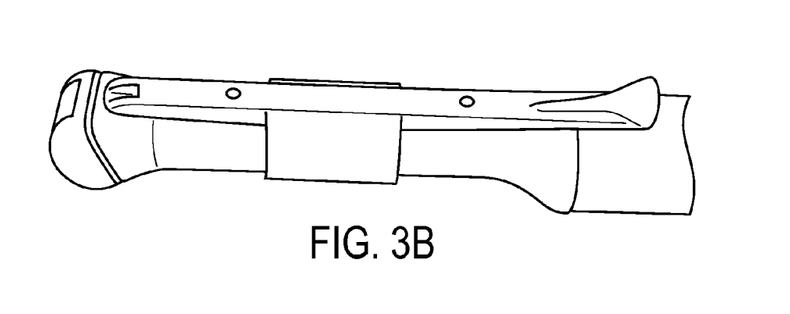
FIG. 3B shows an end-fire TRUS probe with a needle probe holder attachment.
Figure 3C:
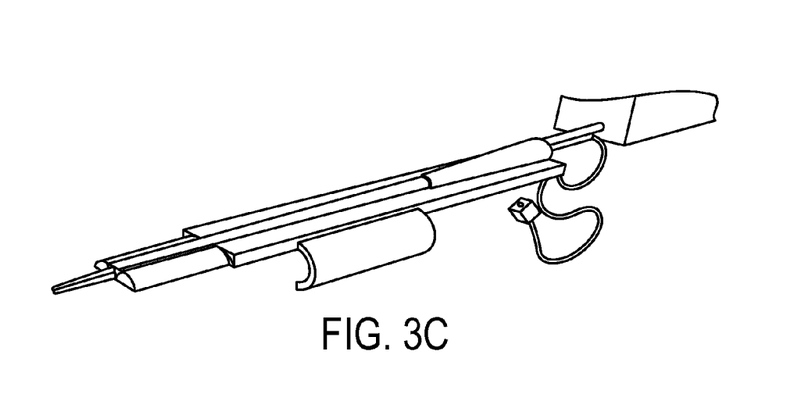
FIG. 3C shows the geometry for the optical attachment comprising a needle and optical fiber.

FIG. 3A is a diagrammatic representation showing the working principle of an embodiment of the invention. FIG. 3A depicts a conventional prostate biopsy procedure where trans-rectal, side-fire ultrasound probe is shown with a biopsy needle. FIG. 3B shows an end-fire TRUS probe with a needle probe holder attachment used in conventional biopsy. FIG. 3C shows the geometry for the optical attachment comprising a needle and optical fiber. The addition of optical fiber would increase the diameter of the hollow channel by only about 2-3 mm relative to a conventional holder comprising only a needle.

Figure 4A:
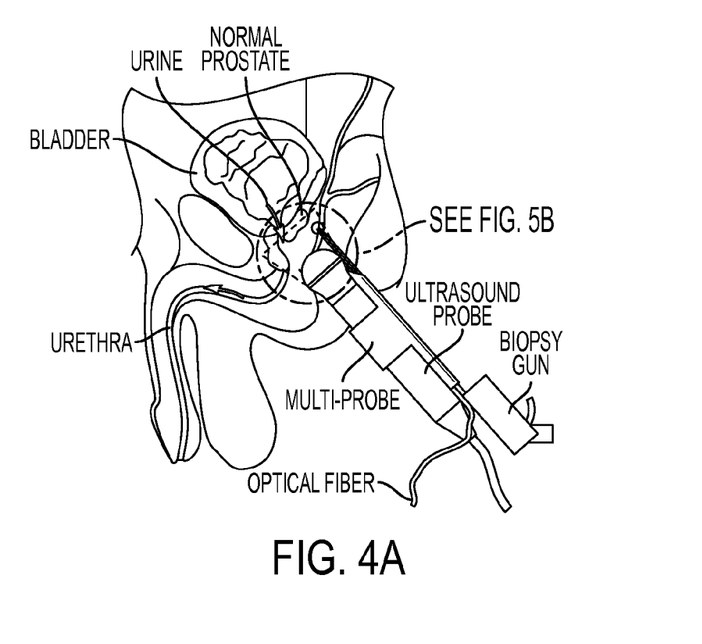
FIG. 4A shows a further view of the probe in use for guiding needle biopsy.
Figure 4B:
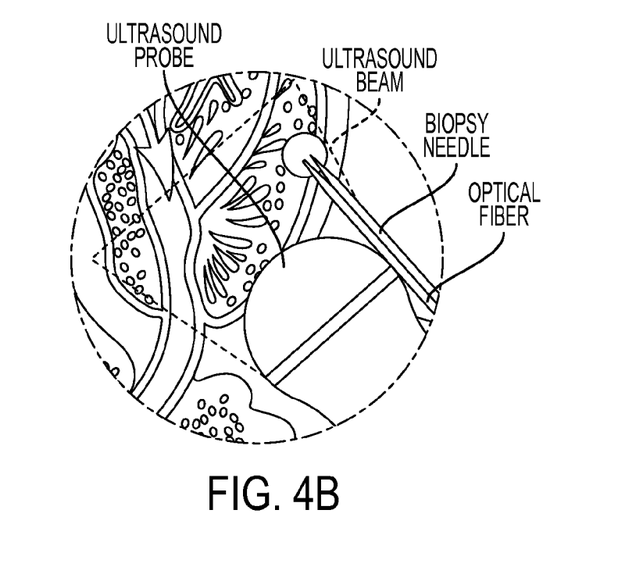
FIG. 4B shows an enlarged view of the probe of the claimed invention in use in diagnosis.

FIG. 4 shows the overall design for the probe device in use. The working procedure can be explained as follows: The multi-modality optical fiber probe on the probe assembly is advanced along the trajectory track using a motorized drive. The optical readings are obtained at various points along the path. For each data point, the white light source delivers the broadband light (300-2000 nm), and the reflected light from the prostate tissue is collected and fed into a CCD spectrometer. The obtained spectrum is then analyzed for calculating absolute values of optical properties of tissue. Similarly, for each data point, auto-fluorescence lifetime is also obtained at multiple emission wavelengths. The collected data is analyzed and presented in real time on the computer screen and a classification algorithm is then utilized to differentiate the cancer tissue from normal tissue. FIG. 4A shows a further view of the probe in use for guiding needle biopsy. FIG. 4B shows an enlarged view of the probe of the claimed invention in use in diagnosis.

In an embodiment of the invention, a motorized computer-controlled probe holder is used to connect the optical attachment with a minaturized step motor that is controlled by computer through a clinician-friendly GUI (graphical user interface) for fast data acquisition and automated probe movement.

Figure 5:
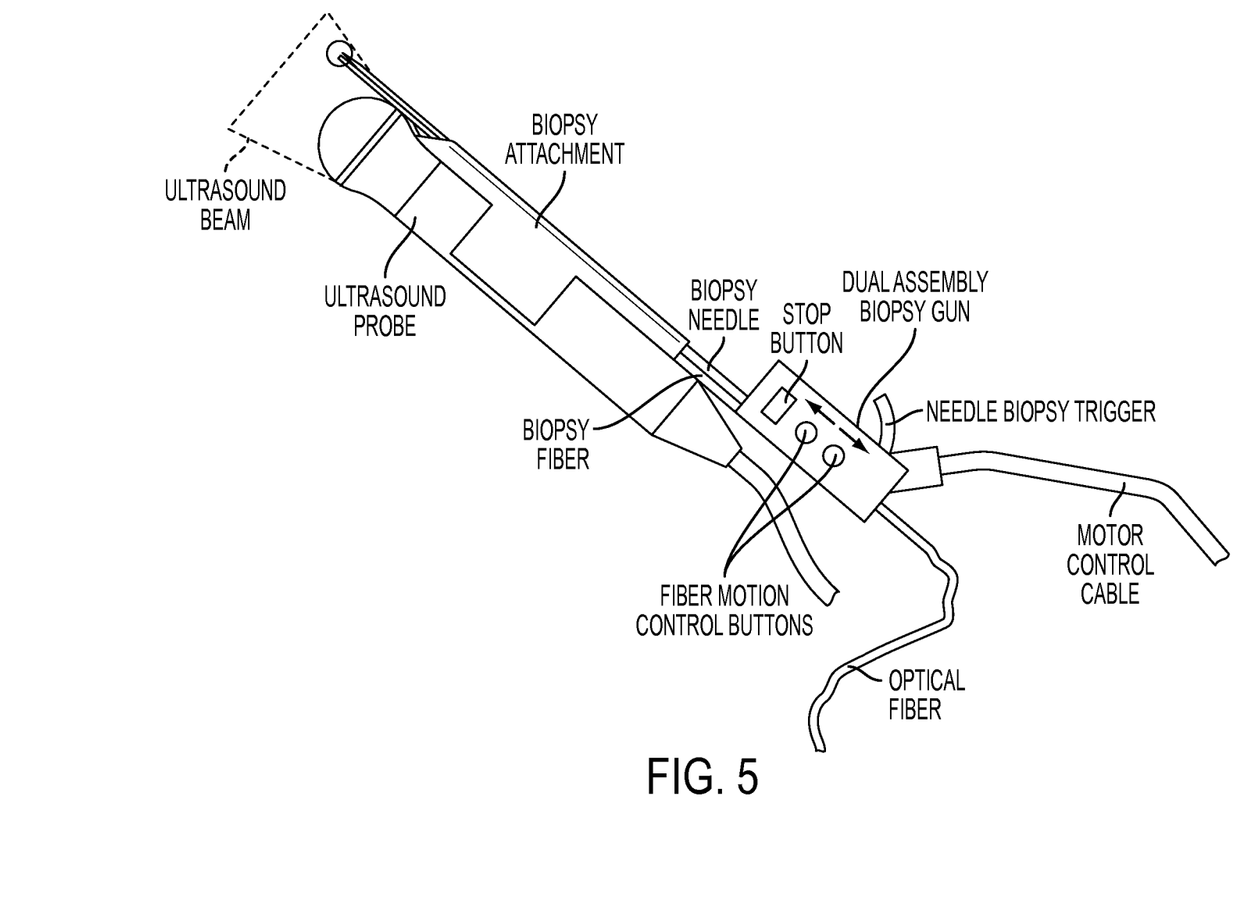
FIG. 5 represents a detailed arrangement of the components of an optical probe of the claimed invention combined with a optical attachment that is removably connected to the probe.

The arrangement in FIG. 5 represents a design of an optically guided prostate biopsy probe. The optical attachment acts as a guide for the biopsy needle and optical fiber. Both the needle and optical fiber are attached to a motorized biopsy gun, which controls the fiber movement/motion and triggers the needle biopsy action.

Working Examples

Animal Model and Preparation

Figure 1:
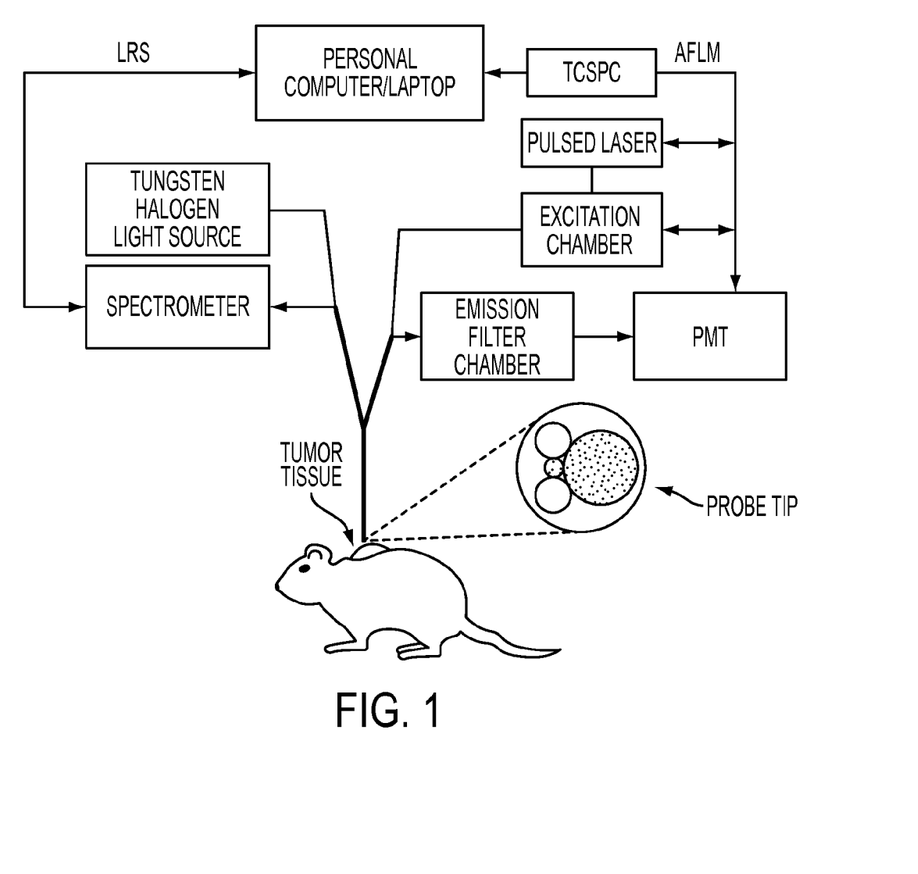
FIG. 1 represents a block diagram illustrating an experimental set-up for a light reflectance spectroscopy (LRS) system (left) and auto-fluorescence lifetime measurement (AFLM) system (right). The latter is based on the time correlated single photon counting method (TCSPC). Measurements were made sequentially, by placing optical fiber tips on the tissue surface. A closer view of bifurcated fiber tips are shown for each fiber (clear=source; filled=detector)

Four one-year old, Copenhagen rats weighing 300-400 g were used in the study. Dunning R 3327 AT3.1 rat prostate carcinoma cells ($\sim 5\times 10^6$) were injected subcutaneously on the fore back of each rat, followed by everyday monitoring of the tumor growth till it reached the volume of ~1.5 cm$^3$. The rat was then anesthetized using a Ketamine/Xylazine combination. Once being anesthetized, the rat had an incision made on the fore back to expose the tumor and a part of normal tissue. The exposed tissue/tumor surface was cleaned by flushing Phosphate Buffered Saline (PBS), followed by multiple optical measurements with a bifurcated optical probe (FIG. 1).

Auto-Florescence Lifetime Measurement

Instrumentation for AFLM

A custom-made, single-channel TCSPC (ISS Inc., Champaign, Ill.) system was employed for auto-florescence lifetime measurements. FIG. 1 on the right panel shows an overall experimental setup for the time domain AFLM. The system consists of a 12-V power supply unit, a stepper motor driving a 5-slot filter wheel for excitation wavelength selection, a continuously variable neutral density (ND) filter for excitation light intensity control, an emission filter, and a highly sensitive cooled PMT (Becker & Hickl GmbH) with a wavelength range between 125-850 nm. The PMT gain was controlled via a PC-based interface board (DCC-100). A broadband (400-1800 nm) pulsed laser (SC-450, Fianium Inc., Eugene, Oreg.) with a pulse width of 5 ps was used as an excitation source at a repetition rate of 20 MHz. The exact synchronization between the laser pulse and the photon detection was achieved through a PC-based single photon counting card (SPC-130). The laser was coupled to the source fiber of the bi-furcated optical probe with a core diameter of 100 μm; resulting fluorescence emission was collected through the detection fiber of a 400-μm core diameter from the other branch of the bi-furcated probe.

AFLM Data Analysis

The auto-fluorescence signals result mainly from Flavins, Lipo-pigments and Porphyrins that introduce optical contrasts to differentiate cancer from healthy tissue. In order to achieve maximum possible auto-fluorescence from all three endogenous compounds, an excitation wavelength of 447 nm was chosen. While keeping the excitation wavelength constant, the emission wavelengths were changed among 532 nm, 562 nm, 632 nm and 684 nm. Filter selection and data collection was made through vender-provided software. The optical probe was placed at ~1 mm away from the surface of the tissue. The in vivo fluorescence data were collected at 5 random positions from the exposed tumor and healthy tissue for each emission wavelength. By the end of the experiment, the animals were sacrificed, and the tumor and healthy tissue were extracted and kept in PBS for ex vivo measurements. Similar data collection procedure was also followed for ex vivo measurements. Thereafter, the detected fluorescence decay curves taken at all tissue positions were imported into Matlab (The Mathworks Inc., Natick, Mass.) and normalized with respect to their peak intensities.

In order to quantitatively differentiate auto-fluorescence decay curves between cancer and control tissue, each curve was fitted by a least square non-linear fitting algorithm, using a two-component exponential model:

$$\text{Intensity}(I) = \sum_i \alpha_i e^{-t/\tau_i} \quad (1)$$

where, $\tau_i$ (i=1, 2) indicates lifetime of each endogenous fluorophore; $\alpha_i$ (i=1, 2) is the intensity contribution of each component to the overall fluorescence decay signal. The confidence interval on each of these four fitted parameters was computed using the "confint" function in Matlab. To count for both fluorophores with their respective weights, a "mean lifetime," $<\tau>$, was calculated using Eq. (2):

$$<\tau> = \frac{\sum_i \alpha_i \times \tau_i^2}{\sum_i \alpha_i \times \tau_i} \quad (2)$$

Light Reflectance Spectroscopy

LRS Instrumentation

LRS system consists of a tungsten-halogen light source (HL2000HP, Ocean Optics, Dunedin, Fla., USA), a CCD-linear-array spectrometer (USB 2000+, Ocean Optics, Dunedin, Fla. USA), and a laptop computer. The spectrometer provided a spectrum ranging from 460 nm-1150 nm. A custom-made, bi-furcated fiber optic probe (Fiberguide Industries, Stirling, N.J., USA) was used, containing two of 100-μm core diameter fibers for both source and detector (s-d)) with a s-d separation of ~110 μm (FIG. 1). The probe was fixed on a stereotactic frame in order to steadily hold the probe in an accurate position and minimize the pressure on the tissue surface. Multiple data points were than obtained by placing the probe at different spatial locations on the tumor tissue and then the normal tissue. On an average, five data points were obtained from in vivo cancer and control tissue. Note that the in vivo LRS measurements were taken after in vivo AFLM readings. Since blood concentration and oxygenation state of hemoglobin in cancer tissue affect LRS greatly, no ex vivo measurement was taken with LRS due to severe alteration in hemodynamic environment from in vivo to ex vivo conditions.

LRS Data Analysis

Each acquired spectrum was divided by a reflectance spectrum obtained from a diffuse reflectance standard (WS-1, Ocean Optics, Dunedin, Fla., USA) to eliminate spectral effects from the source, fibers and detector. Then, the spectral range from 500 nm-850 nm was selected; a reflectance model, as shown in Eq. (1), was used to obtain absolute values of the concentrations of oxy-hemoglobin ([HbO]), deoxy-hemoglobin ([HbR]) and total hemoglobin ([HbT]=[HbR]+[HbO]), along with the reduced scattering coefficient ($\mu_s'$), $$R(\lambda) = \frac{\mu_s'(\lambda)}{k_1 + k_2 \cdot \mu_a(\lambda)} \quad (1)$$

where, R is the measured reflectance, $\mu_s'(\lambda)$ is the reduced scattering coefficient, $\mu_a$ is the absorption coefficient depending on the concentration of hemoglobin derivatives, and $k_1$ and $k_2$ are instrument-based parameters that depend only on the probe geometry and hardware set-up. A detailed description of methodology to obtain the system-dependent parameters has been previously published[21]. Briefly, at first, $k_1$ and $k_2$ were calculated for the fiber optic probe using tissue-phantom calibration. Then, an optimization routine (ant colony optimization) was used to fit the parameters of $\mu_s'$, [HbO] and [HbR], to optimally match the measured reflectance. The data processing was done using a code implemented in Matlab.

Because of a small s-d separation, the area of optical interrogation by this 200-μm probe is relatively small. It is possible that at certain locations, the probe can be on top of a large blood vessel, causing the reflectance signal to nearly diminish in 500-600 nm range due to high optical absorption of hemoglobin. Such spectra were identified and excluded as outliers in the data analysis. Overall, the dataset included five measurements in each tissue type (cancer and control) for rats 2 and 4, and four measurements each for rat 3.

Results

Figure 6:
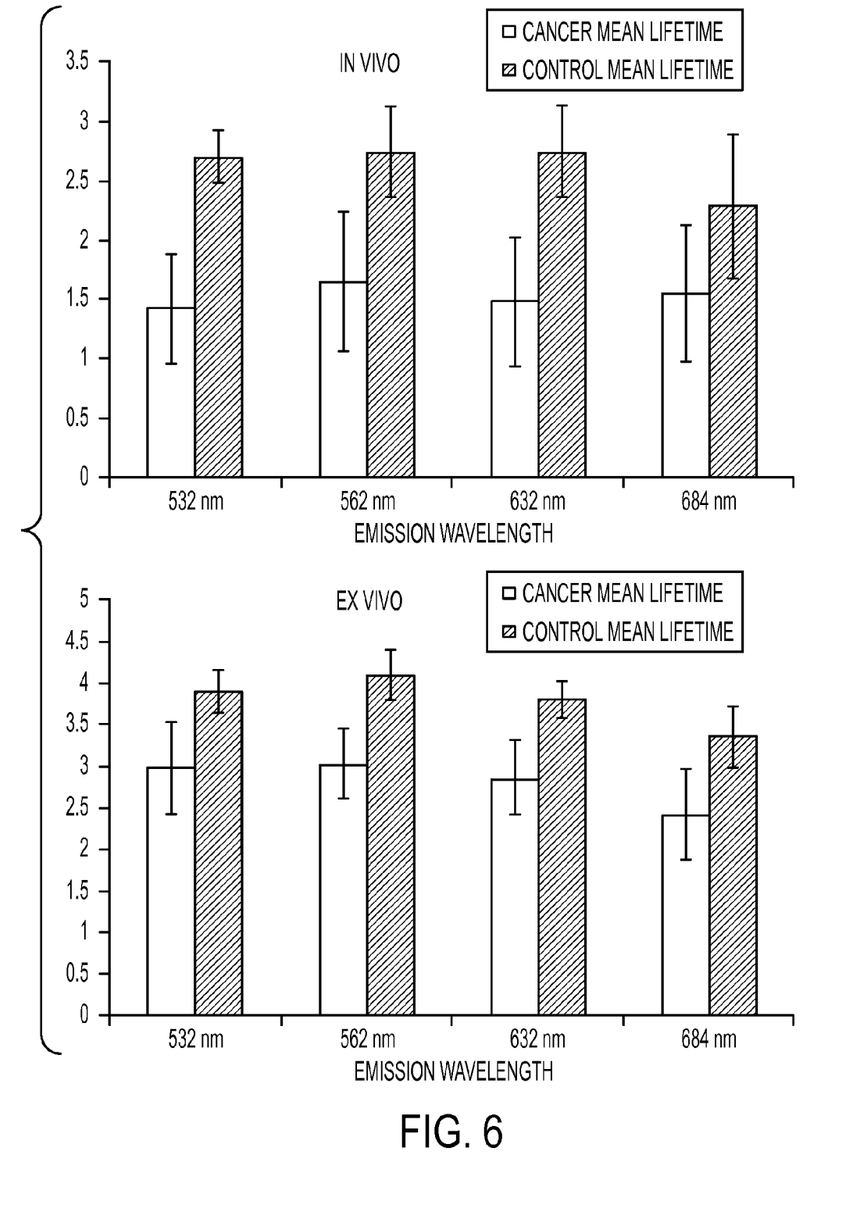
FIG. 6 shows a comparison of mean lifetime for (A) in vivo measurements and (B) ex vivo measurements (n=20)

The mean lifetime calculated at each emission wavelength was averaged over all 4 rats. FIGS. 6A and 6B show the comparison for averaged mean lifetime with standard deviation for in vivo and ex vivo measurements, respectively. It can be noticed from the plots that the averaged mean lifetime from cancer is lower than that from normal tissue in both cases at all emission wavelengths, as summarized in Table 1. This table also contains p-values that were obtained using a mixed model repeated measures ANOVA between the cancer and normal group. In addition, the average mean lifetime over 4 emission wavelengths were found to be 1.52±0.09 ns and 2.61±0.22 ns for in vivo cancer and control, respectively. As comparison, ex vivo measurements result in the averaged mean lifetime values of 2.82±0.27 ns and 3.78±0.31 ns for cancer and control, respectively. In order to see the effects of tissue degradation on mean lifetime, a mixed model repeated measures ANOVA was performed between in vivo and ex vivo groups, revealing a significant difference between them.

TABLE I

Summary for in vivo and ex vivo auto-fluorescence mean lifetimes.

| | | Emission Wavelength (nm) | | | |
|---|---|---|---|---|---|
| | | 532 | 562 | 632 | 684 |
| In vivo lifetime (ns) | Cancer | 1.43 | 1.65 | 1.48 | 1.55 |
| | Control | 2.7 | 2.74 | 2.74 | 2.29 |
| | P-value | $2.85 \times 10^{-13}$ | $5.70 \times 10^{-8}$ | $9.04 \times 10^{-11}$ | $2.0 \times 10^{-4}$ |
| Ex vivo lifetime (ns) | Cancer | 2.98 | 3.02 | 2.86 | 2.84 |
| | Control | 3.9 | 4.1 | 3.81 | 3.35 |
| | P-value | $5.85 \times 10^{-8}$ | $3.54 \times 10^{-9}$ | $1.01 \times 10^{-10}$ | $4.87 \times 10^{-7}$ |

FIG. 7 shows the results of four parameters derived through LRS. The spectra were averaged over multiple points of each tissue type (either cancer or control) from each rat, and standard error of mean (SEM, represented by error bars) was calculated and shown. The values of [HbO] and [HbT] exhibit an increase in concentration in the tumor tissue as compared to the normal tissue in all 3 rats. The values of [HbR], on the other hand, were found to be very small compared to those of [HbO], and the standard error was relatively higher. Furthermore, the values of $\mu_s'$ were found to be smaller with a relatively small SEM in tumor tissue, as compared to those in the normal tissue. A mixed model ANOVA analysis for repeated measures revealed significant differences between tumor and normal tissue in [HbO] (p=0.03), [HbT] (p=0.03), and $\mu_s'$ (p=0.01). Difference in [Hb] was found to be insignificant with p-value of 0.22.

In order to evaluate whether any of the parameters hold potential to be used as an intrinsic biomarker, we employed support vector machine (SVM) as a classification algorithm. In our approach, first, we chose any two independent parameters from the list of the fitted parameters, such as four mean lifetimes at the four emission wavelengths, [HbO], [HbT], and light scattering coefficient, as classifiers; second we utilized the leave-one-out cross validation method to determine the sensitivity and specificity for the chosen paired classifiers. Since more than two parameters were available as classifiers, we used various combinations of parameters (see Table II) to examine which pairs of parameters could be selected as best classifiers. For AFLM, with 20 data points available in each category (tumor and control) for testing, we obtained perfect sensitivity and specificity of 100% for all possible pairs in wavelength combinations. Table II lists only a couple of wavelength pairs as an example. If we considered the data from LRS, which had 14 data points available in each category, the best pair chosen as classifiers were determined to be [HbO] and $\mu_s'$ at 750 nm, which gave rise to both sensitivity and specificity of 92.86%.

TABLE II

Sensitivity and specificity values calculated for different pairs of obtained parameters using two modalities

| | Classification Parameters | | | | |
|---|---|---|---|---|---|
| | LRS (n = 14) | | | AFLM (n = 20) | |
| | [HbO] and [HbT] | $\mu_s'$ (750 nm) and $\mu_s'$ (830 nm) | [HbO] and $\mu_s'$ (750 nm) | 532 nm and 562 nm | 632 nm and 684 nm |
| Sensitivity (%) | 71.43 | 78.57 | 92.86 | 100 | 100 |
| Specificity (%) | 71.43 | 92.86 | 92.86 | 100 | 100 |

Figure 7A:
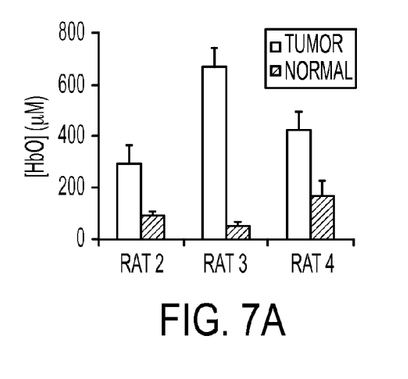
FIG. 7A-7D shows a comparison of (A) [HbO], (B) [HbR], (C) [HbT], and (D) $\mu_s'$ values at 750 nm derived from in vivo rat tumor tissue and control tissue with LRS.
Figure 7B:
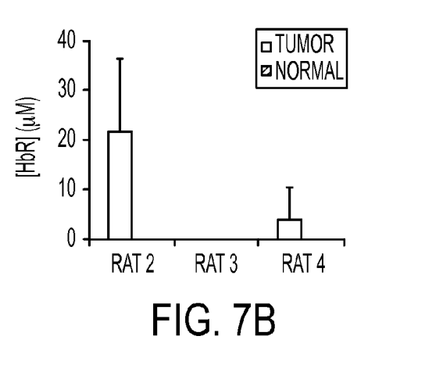
Figure 7C:
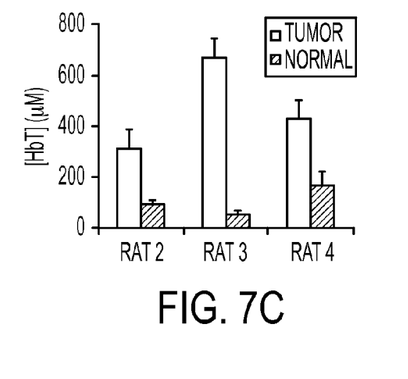
Figure 7D:
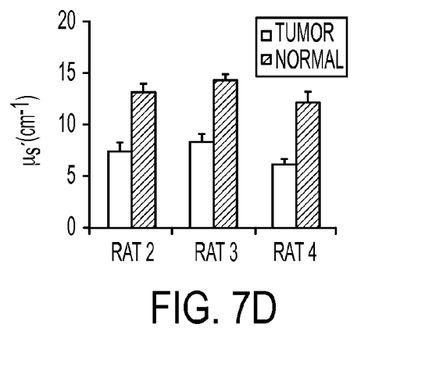

The above results demonstrate the feasibility of using LRS and AFLM as independent techniques for differentiating rat cancer tissue from normal tissue. Several optical parameters were obtained which could serve as potential biomarkers to identify cancerous tissue. Specifically, FIGS. 7A and 7B present significant differences in mean lifetime between cancer and non-cancerous tissue. Such results are expected since AFLM may be able to sense changes in temperature, pH, oxygen content and nutrient supply of the measured tissue. Because of such good sensitivity to local tissue environment, AFLM was found to be very robust, with 100% sensitivity and specificity when the mean lifetimes from any two wavelengths out of the four emission wavelengths were selected to classify cancer from normal tissue. Table II shows examples of two groups of wavelength combinations. The results also suggest difference in absolute lifetime values between in vivo and ex vivo measurements, while both cases exhibit a similar trend, namely, mean lifetime values were higher in normal tissues than those in cancerous tissues. This set of observation is also expected because rat tumor ex vivo samples may have experienced alternations in their physiological, metabolic and biochemical condition, as compared to in vivo tissue, while being kept in PBS and measured ~10 hours after the extraction.

In case of LRS, an increase in total blood concentration was found; it is indicative of increased vasculature of tumor tissue (FIG. 7) as compared to normal tissue. It was also found that in most cases, [HbR] levels were very low, indicating a very high level of hemoglobin oxygen saturation (~99%). This could be partially attributed to the fact that the optical readings were taken on the surface of the tissue which was exposed to room air. For deeper tumor regions, we may expect higher values of [HbR] as tumors are generally known to be hypoxic. Furthermore, light scattering, which is closely associated with cell size and morphology, was found to be significantly different between tumor and normal tissues. This set of results is also expected as cell size and morphology are known to be different in cancerous cells compared to normal cells. It was further observed that $\mu_s'$ variability was relatively low at the individual level (indicated by error bars in FIG. 7), and that the $\mu_s'$ values were well significantly separated between the cancer and control groups, as indicated by a lower p value of 0.01. To further increase the understanding of relation between $\mu_s'$ and cell morphology, and in turn to be used for cancer staging, we plan to include pathological analysis along with the optical quantification in our near future studies.

While AFLM seems to be able to optimally determine or detect rat prostate cancer with perfect sensitivity and specificity, we are prepared to have a dual-modality approach to increase an improved detection power. This is because human prostate is quite different from a solid rat tumor and often has multi-focal cancer lesions with different levels of cancer stage. It is highly possible that AFLM alone may not be able to clearly identify low-grade prostate cancer lesions, and a second detection modality, such as LRS, may provide a complementary solution.

To mimic real biopsy environments in the animal model, where the tissue is not directly exposed to room air and background auto-fluorescence may exist, a motorized system is planned to be implemented in order to drive the optical fiber into the tumor region in a minimally invasive manner with an appropriate step size. Also, use of orthotopic animal models of prostate cancer can be an alternative option when investigating realistic tissue biopsy procedures.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An apparatus for detection of cancer by optical biopsy, the apparatus comprising:
    a motorized computer-controlled probe holder comprising a probe device, wherein the probe device comprises an integrated transrectal ultrasound (TRUS) probe and an optical attachment wherein the optical attachment is controlled by the motorized computer-controlled probe holder, and wherein the optical attachment comprises at least one optical fiber, at least one biopsy needle, and at least one detector unit, and further wherein the detector unit is adapted to perform light reflectance spectroscopy, auto-fluorescence spectroscopy and auto-fluorescence life time measurements;
    at least two light sources; and
    a spectrometer.

2. The apparatus of claim 1, further comprising a miniaturized step motor connected to the optical attachment and controlled by a computer with a user friendly graphical user interface (GUI) for data acquisition and automated probe movement.

3. The apparatus of claim 1, wherein the optical fiber and the biopsy needle are located within a hollow channel of the optical attachment.

4. The apparatus of claim 1, wherein the optical fiber and the biopsy needle are separable from one another.

5. The apparatus of claim 1, wherein the optical fiber is a bifurcated fiber comprising at least one source channel and at least one detector channel.

6. The apparatus of claim 5, wherein the source channel has a diameter ranging from 100 to 200 µm.

7. The apparatus of claim 5, wherein the detector channel has a diameter ranging from 200 to 400 µm.

8. A system for imaging of tissue, said system comprising a probe device, wherein the probe device comprises an integrated in vivo ultrasound probe and an optical attachment, wherein the optical attachment comprises at least one optical fiber, at least one biopsy needle, and at least one detector unit, and further wherein the detector unit is adapted to perform light reflectance spectroscopy, auto-fluorescence spectroscopy and auto-fluorescence life time measurements;
    at least two light sources; and
    a spectrometer.

9. The system according to claim 8, wherein said system is used for locating and diagnosing a lesion in a tissue in an anatomical structure in vivo.

10. The system according to claim 8, wherein said system is used for guiding a biopsy of a lesion in a tissue in an anatomical structure in vivo.

* * * * *